(12) United States Patent
Bates (10) Patent No.: US 6,510,918 B2
(45) Date of Patent: Jan. 28, 2003

(54) COMBINED STETHOSCOPE AND REFLEX HAMMER

(76) Inventor: Ronald J. Bates, 2860 Neely St. Apt. 206, Batesville, AR (US) 72501

( * ) Notice: Subject to any disclaimer, the term of this patent is extended or adjusted under 35 U.S.C. 154(b) by 31 days.

(21) Appl. No.: 09/845,797

(22) Filed: Apr. 30, 2001

(65) Prior Publication Data

US 2002/0157896 A1 Oct. 31, 2002

(51) Int. Cl.[7] ................................................. A61B 7/02
(52) U.S. Cl. ....................... 181/131; 181/126; 600/528; 600/553
(58) Field of Search .................... 181/131, 129, 181/130, 126; 381/67; 600/528, 553; D24/134, 142

(56) References Cited

U.S. PATENT DOCUMENTS

| | | | |
|---|---|---|---|
| 1,913,780 A | | 6/1933 | Wappler |
| 2,532,093 A | * | 11/1950 | Golub et al. ................. 600/553 |
| 2,566,687 A | | 9/1951 | Wehby |
| 2,908,268 A | * | 10/1959 | Guest .......................... 600/553 |
| 3,344,781 A | * | 10/1967 | Allen .......................... 600/553 |
| D243,717 S | | 3/1977 | Edmark et al. |
| 4,147,163 A | | 4/1979 | Newman et al. |
| 4,475,619 A | * | 10/1984 | Packard ...................... 181/137 |
| 4,580,198 A | | 4/1986 | Zinnanti, Jr. |
| 4,672,975 A | | 6/1987 | Sirota |
| 4,802,550 A | * | 2/1989 | Poore .......................... 181/131 |
| 5,663,533 A | * | 9/1997 | Judge .......................... 181/131 |
| 5,920,038 A | * | 7/1999 | Foster ......................... 181/131 |
| 5,989,186 A | | 11/1999 | Alatriste |
| 6,406,436 B1 | * | 6/2002 | Schiffman ................... 600/553 |
| 6,454,045 B1 | * | 9/2002 | Ryan .......................... 181/131 |

FOREIGN PATENT DOCUMENTS

| | | | | |
|---|---|---|---|---|
| CN | 1073352 A | * | 6/1993 | ............ A61B/9/00 |
| DE | 3771847 A1 | * | 9/1991 | ............ A61B/3/00 |
| EP | 0269048 A1 | | 6/1988 | |
| GB | 2221535 A | * | 2/1990 | ............ G01B/3/00 |
| RU | 2050829 C1 | * | 12/1995 | ............ A61B/7/02 |

* cited by examiner

*Primary Examiner*—Robert E. Nappi
*Assistant Examiner*—Edgardo San Martin
(74) *Attorney, Agent, or Firm*—Ray F. Cox, Jr.

(57) ABSTRACT

A combined stethoscope and reflex hammer. Preferably, the head of the reflex hammer is incorporated into an o-ring securing the diaphragm membrane of the stethoscope chest piece so that a standard stethoscope may be easily retrofitted to add the reflex hammer function. A rigid handle for the reflex hammer is provided by a penholder rigidly affixed to the stethoscope in proximity to the chest piece. The pen may be provided with a penlight so that the combined instrument also provides that function in addition to providing a writing pen, a reflex hammer and a stethoscope.

7 Claims, 8 Drawing Sheets

COMBINED STETHOSCOPE AND REFLEX HAMMER

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to medical examination instruments, and in particular, to such instruments capable of providing several examination functions in a single instrument.

2. Brief Description of the Related Art

A physician will normally carry a stethoscope, a reflex hammer and a pen for making notes. In addition, the physician will often carry a penlight. While a stethoscope may be carried around the neck of the physician, the stethoscope as well as the other instruments are often carried in the pocket of a lab coat and are subject to being mislaid and otherwise unavailable when needed.

Information relevant to attempts to address these problems can be found in the following described U.S. and foreign patents. However, each of these references suffers from one or more disadvantages.

European Patent No. EP269,048 discloses a stethoscope that incorporates a hammer head and a built-in lamp with battery and switch which can be provided in the head of the stethoscope. The stethoscope includes a handle attached to the head of the stethoscope by a threaded section. An incandescent lamp is built into the head of the stethoscope. Reflex hammer heads are inserted into both sides of the chest piece of the stethoscope. This European patent thus discloses a reflex hammer incorporated into the head of a stethoscope and also discloses a handle attached to the stethoscope and a lamp incorporated into the stethoscope. The European patent does not disclose a reflex hammer incorporated into an o-ring for attaching the diaphragm to the chest piece of a stethoscope nor does it disclose a handle in the form of a penholder.

Other patents that disclose attempts to solve the problem of multiple instruments carried by an examining physician are found in the following patents:

U.S. Pat. No. 5,989,186 discloses a stethoscope in which the head has a cover which includes a membrane (or diaphragm) over the opening of the head of the stethoscope. The cover incorporates a casing which has a light source. The casing is adapted for mounting various instruments, such as an otoscope or opthalomoscope. In one embodiment, the casing is mounted to the flexible tubing of the stethoscope by clamps.

U.S. Pat. No. 4,580,198 discloses an illuminator carried on an examination scope. U.S. Pat. No. 2,566,687 discloses a stethoscope in which the head is combined with a light and tongue depressor. U.S. Pat. No. 4,672,975 discloses a stethoscope with an electronic device which forms the image of a beating heart on a display. U.S. Pat. No. 4,147,163 discloses a battery handle for an electrically illuminated diagnostic instrument. U.S. Pat. No. 1,913,780 discloses an illuminating attachment for a speculum for oral, rectal or vaginal examination. U.S. Design Pat. No. Des.243,717 appears to show a stethoscope in which the body with the diaphragm and bell is replaced with another instrument, perhaps electronic.

These limitations of the prior art are overcome by the present invention as described below.

BRIEF SUMMARY OF THE INVENTION

The present invention is directed to an apparatus that satisfies the need for a combined examination instrument which includes all the functions normally required by an examining physician or other medical professional for the examination of a patient.

In the present invention, the problems and limitations of the prior art devices are avoided and greater efficiency introduced into the physician's routine activities by combining the stethoscope and reflex hammer into a single instrument with an integral handle that also serves as a pen holder. A modem stethoscope includes two ear pieces which are secured to flexible rubber tubing by a yoke. The flexible rubber tubing is attached to a chest piece. The chest piece comprises a diaphragm portion and a bell portion. The diaphragm portion typically includes a membrane, i.e., a thin piece of plastic material, which is held in place by an o-ring that slips over a metal rim of the bell-shaped diaphragm portion. The diaphragm portion in turn communicates with a tube to the bell portion of the chest piece. This communicating tube communicates at right angles to another short length of metal connecting tube which in turn fastens to the end of the flexible rubber tubing.

In the preferred form of the invention, the head of the reflex hammer is incorporated into the o-ring so that a stethoscope may be easily retrofitted to add the reflex hammer function. In order to completely convert the stethoscope for use as a reflex hammer, it is necessary to provide a rigid handle, since the rubber tubing of the stethoscope is too flexible to serve this function. Accordingly, in the preferred embodiment of the invention, a penholder is rigidly affixed to the stethoscope in proximity to the chest piece, for example, by a clamp around the connecting tube. The pen and penholder then provide the handle for the reflex hammer.

As an added feature, the pen may be provided with a penlight so that the combined instrument also provides that function in addition to providing a writing pen, a reflex hammer and a stethoscope.

It is therefore an object of the present invention to provide for a combined examination instrument which includes all the functions routinely required by an examining physician or other medical professional for the examination of a patient.

It is a further object of the present invention to provide for such an instrument in which the head of the reflex hammer is incorporated into the o-ring affixing the diaphragm membrane to the chest piece so that a stethoscope may be easily retrofitted to add the reflex hammer function.

It is also an object of the present invention to provide for such an instrument in which a penholder is rigidly affixed to the stethoscope in proximity to the chest piece so that the pen and penholder when held in conjunction with the flexible tubing then provide the handle for the reflex hammer.

It is a still further object of the present invention to provide for such an instrument with a penlight so that the combined instrument also provides that function in addition to providing a writing pen, a reflex hammer and a stethoscope.

These and other features, objects and advantages of the present invention will become better understood from a consideration of the following detailed description of the preferred embodiments and appended claims in conjunction with the drawings as described following:

BRIEF DESCRIPTION OF THE SEVERAL VIEWS OF THE DRAWINGS

FIGS. 8–11 illustrate an embodiment of the penholder having an elastic section with a slit along one side for elastically gripping the flexible tubing.

FIGS. 12–15 illustrate another embodiment of the penholder wherein the penholder is attached to the flexible tubing by means of one or more hinged clamps which engage the penholder and the flexible tubing and are held together by adhesive pads.

FIGS. 16–19 illustrate an embodiment in which the penholder is affixed to the flexible tubing by means of a single hinged clamp which fits over the penholder and flexible tubing and is fastened by adhesive pads.

FIG. 18 also shows that additional adhesive pads may be arrayed along the insides of the hinged clamp so as to adhesively attach to the penholder and flexible.

FIGS. 20–22 illustrate an alternative embodiment in which the hinged clamp is fastened by a snap-on clip.

DETAILED DESCRIPTION OF THE INVENTION

Figures 1, 2:
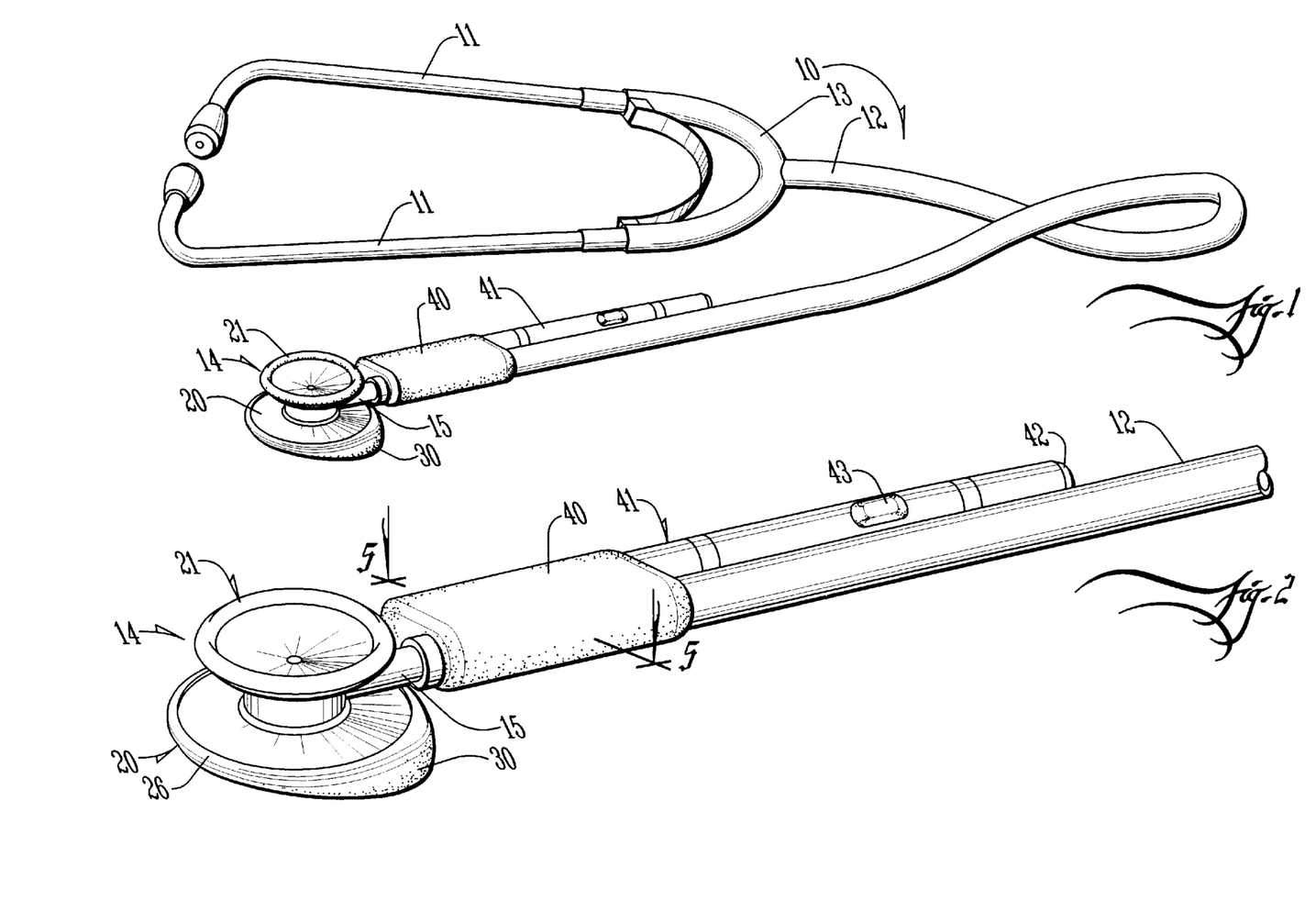
FIG. 1 is a perspective view of a stethoscope as modified by the present invention.
FIG. 2 is a partial enlarged perspective view of the stethoscope of FIG. 1 showing the stethoscope chest piece fitted with an o-ring incorporating a reflex hammer head. A handle comprising a penholder and pen is also provided.
Figures 3, 4:
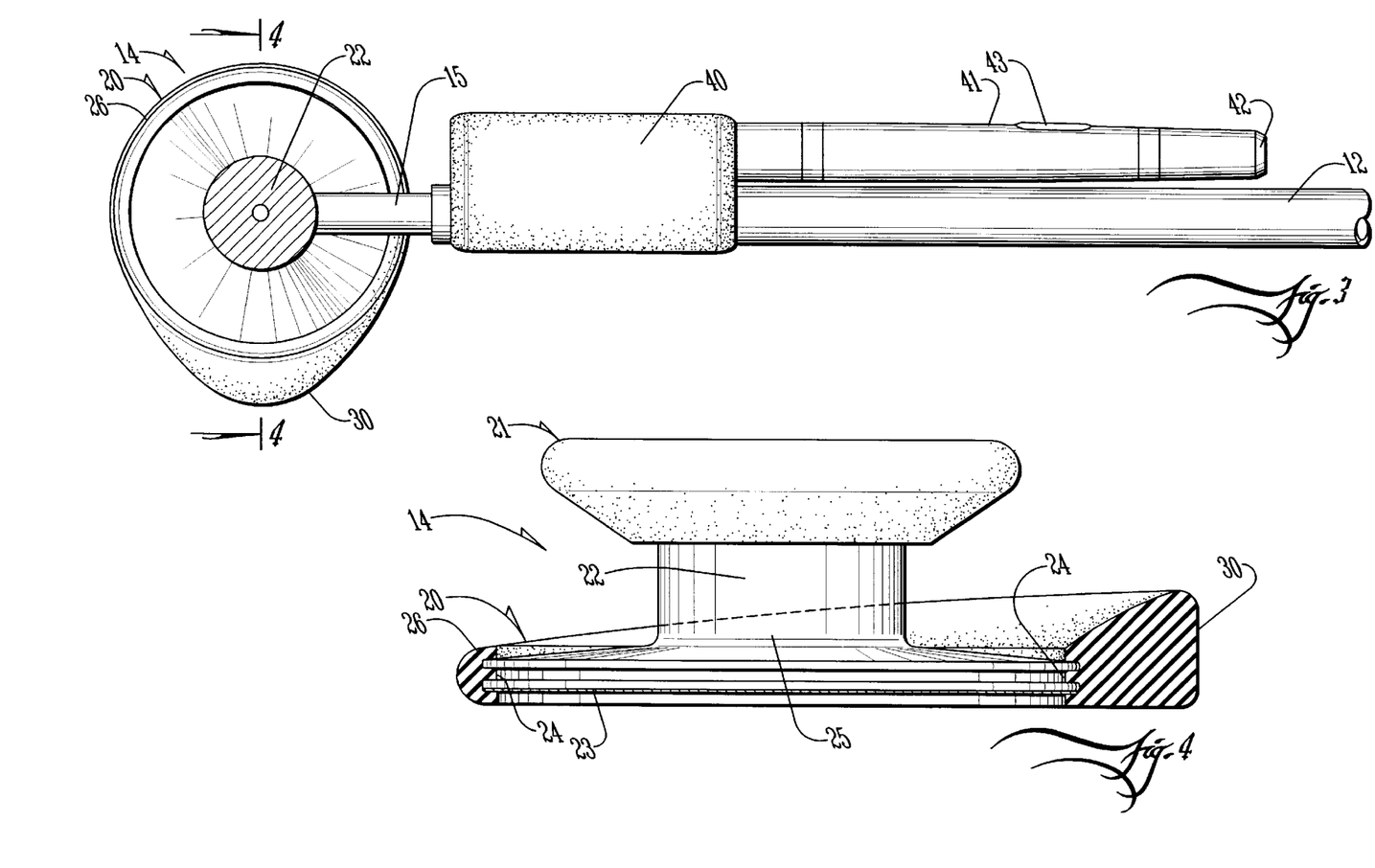
FIG. 3 is a top plan sectional view of the partial stethoscope of FIG. 2. The bell portion of the chest piece is removed for clarity.
FIG. 4 is a sectional view of the chest piece with the o-ring sectioned along the line 4—4 of FIG. 3.
Figure 6:
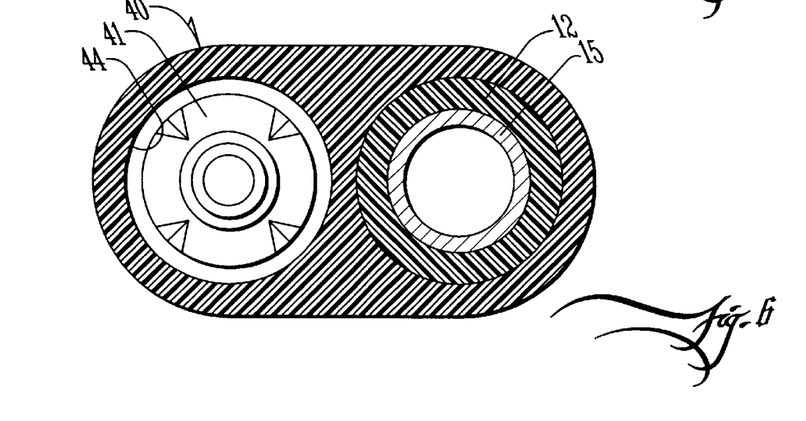
FIG. 6 is a sectional view of the penholder and pen taken along the line 6—6 of FIG. 5.
Figure 7:
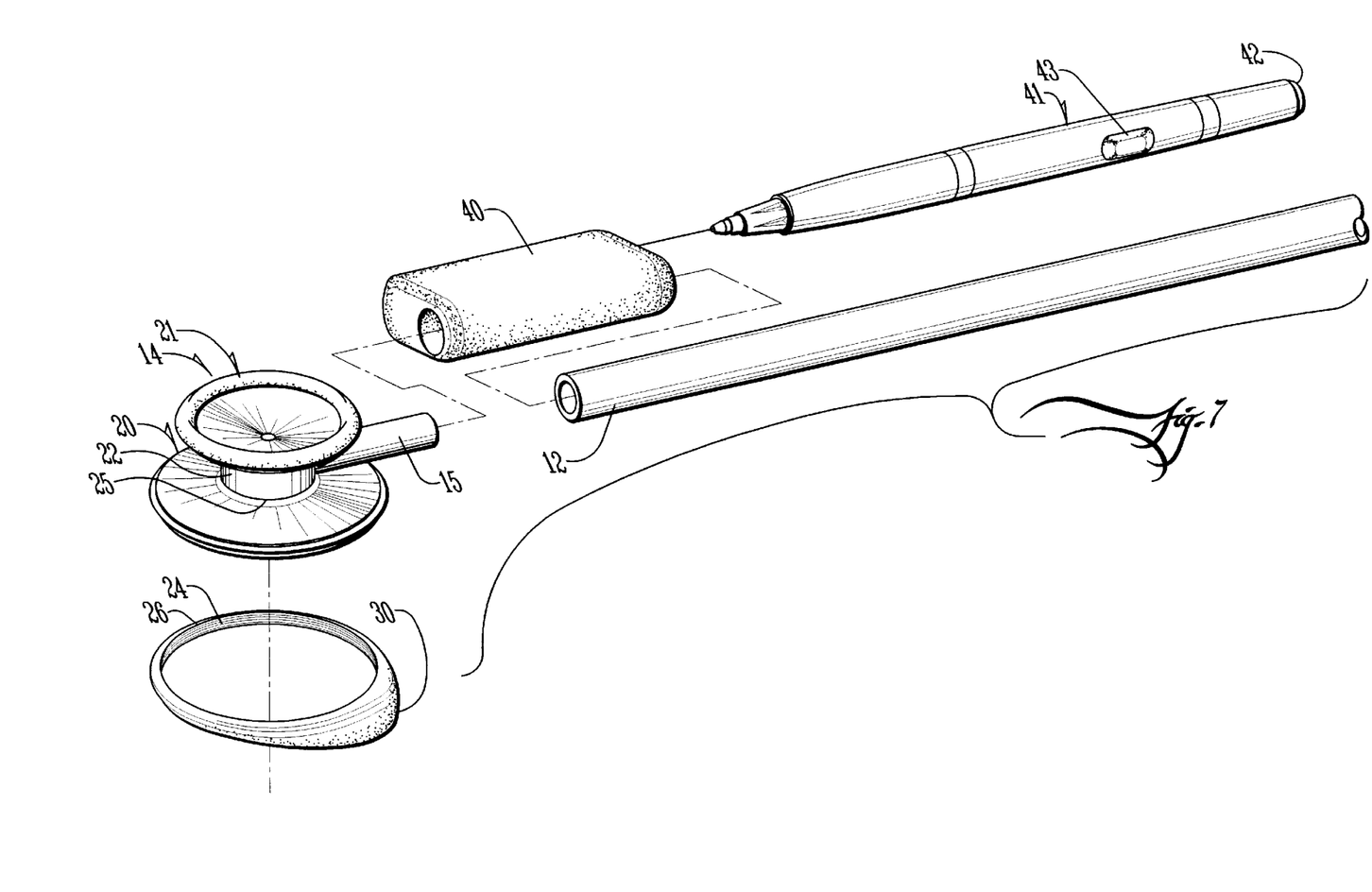
FIG. 7 is an exploded perspective view of the partial stethoscope of FIG. 1 showing the assembly of the penholder to the chest piece and tubing and insertion of the pen in the penholder.
Figures 8, 9, 10, 11:
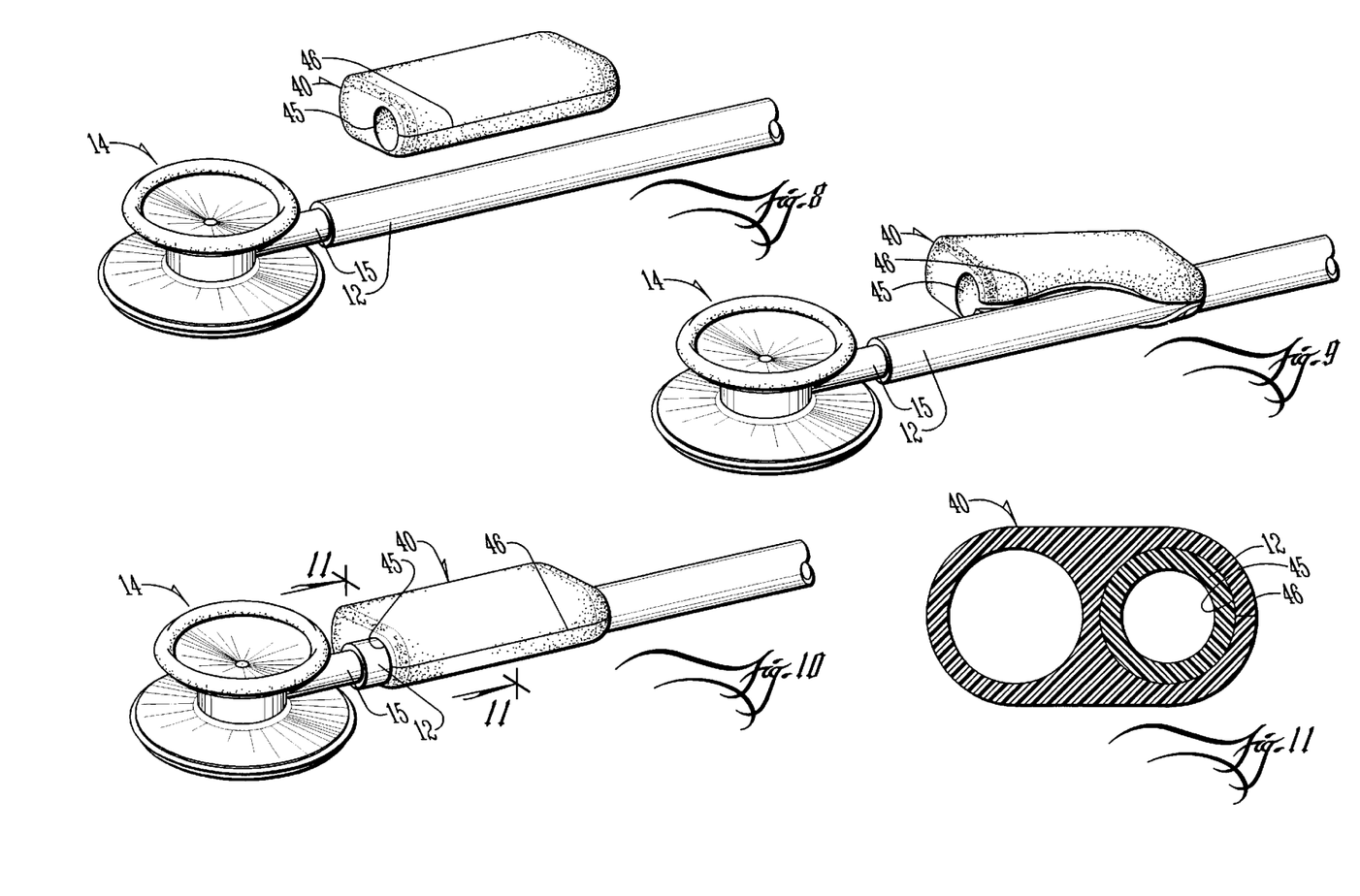
FIG. 8 is an exploded perspective view of the chest piece and this embodiment of the penholder.
FIG. 9 is a perspective view of the penholder of FIG. 8 being engaged to the flexible tubing.
FIG. 10 is a perspective view of the penholder of FIG. 8 assembled to the flexible tubing.
FIG. 11 is a sectional view of the penholder assembled to the flexible tubing of FIG. 10 taken along the line 11—11 of FIG. 10.
Figure 12:
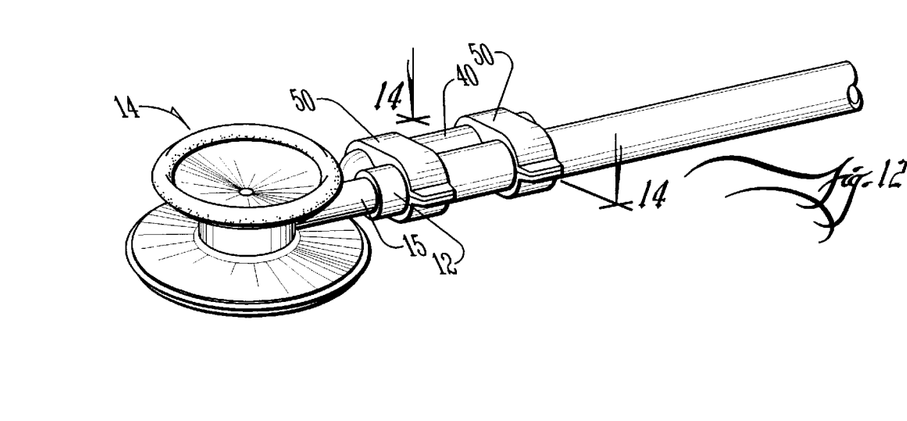
FIG. 12 is a perspective view of the chest piece and penholder where the penholder is affixed to the flexible tubing by two hinged clamps.
Figure 13:
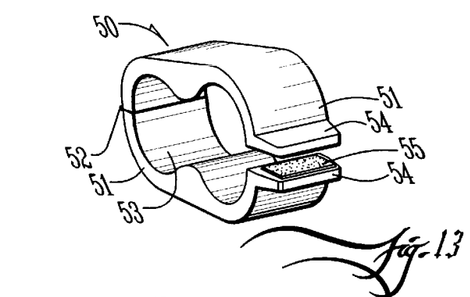
FIG. 13 is perspective view of the hinged clamp.
Figure 14:
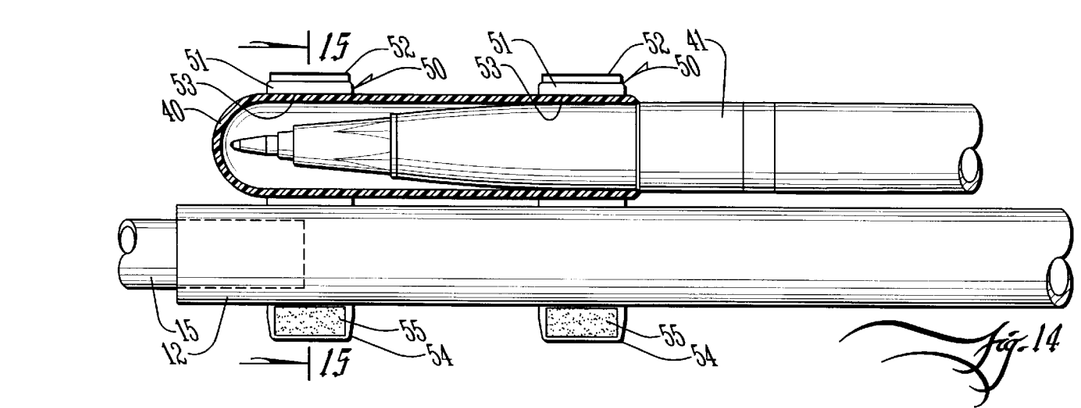
FIG. 14 is a top plan view of the penholder and hinged clamps of FIG. 12 sectioned along the line 14—14 of FIG. 12.
Figure 15:
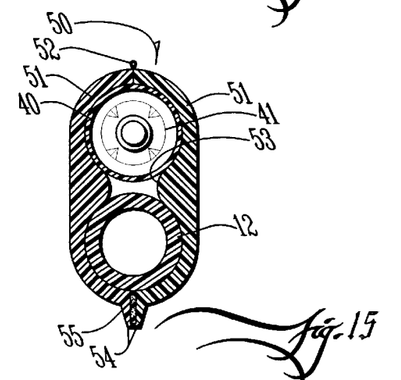
FIG. 15 is a sectional view of the penholder and hinged clamp of FIGS. 12 and 14 sectioned along the line 15—15 of FIG. 14.
Figures 16, 17, 18, 19:
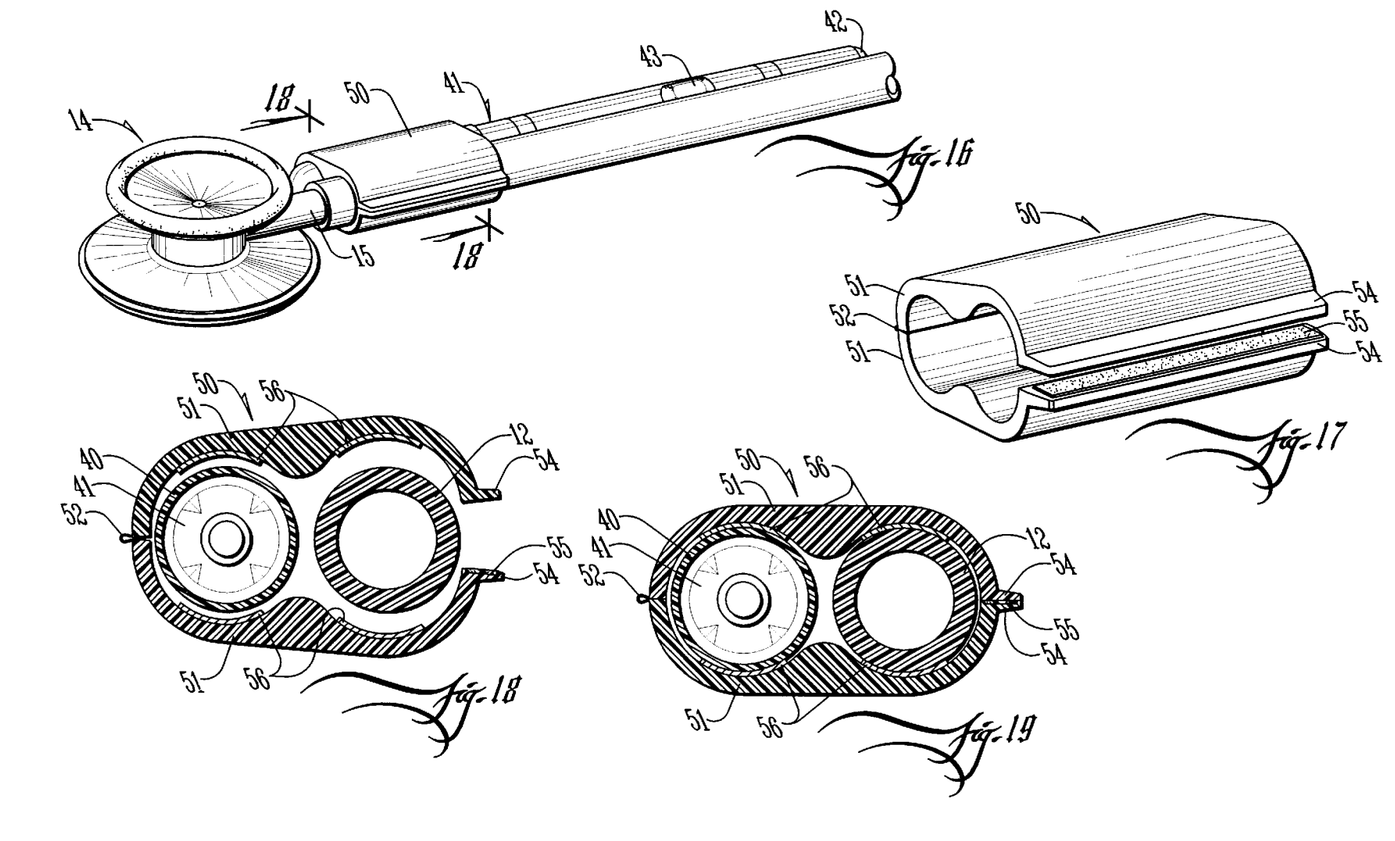
FIG. 16 is a perspective view of the penholder assembled to the flexible tubing by a single hinged clamp.
FIG. 17 is a perspective view of the hinged clamp illustrating how the adhesive pads may be disposed along a first flange whereby the first flange is adhesively fastened to a second flange.
FIG. 18 is a sectional view along the line 18—18 of FIG. 16 showing the assembly of the partially open hinged clamp to the penholder and flexible tubing.
FIG. 19 is the sectional view of FIG. 18 showing the hinged clamp in a closed position.

The preferred embodiment of the invention is described with reference to FIGS. 1–7. In particular, with reference to FIG. 1, a typical stethoscope 10 includes two ear pieces 11 which are secured to flexible rubber tubing 12 by a yoke 13. The flexible rubber tubing 12 is attached to a chest piece 14 by slipping the end of the rubber tubing 12 over a connecting tube 15 as shown in FIG. 6. As shown in FIGS. 2 and 4, the chest piece 14 comprises a diaphragm portion 20 and a bell portion 21. The diaphragm portion 20 typically includes mouth 25 covered by a membrane 23, i.e., a thin piece of plastic material. The membrane 23 is held in place over the mouth 25 by an elastic o-ring 26 which slips over a metal rim 24 surrounding the mouth 25. The diaphragm portion 20 communicates with a communicating tube 22 to the bell portion 21 of the chest piece 20. The communicating tube 22 communicates at right angles to another short length of metal connecting tube 15 which, as described above, in turn fastens to the end of the pliable rubber tubing 12. It should be understood that the chest piece 14, including the bell portion 21, diaphragm portion 20, communicating tube 22, and connecting tube 15 together constitute a single rigid structure.

In the preferred form of the invention, the stethoscope 10 incorporates the functions of a reflex hammer. The diaphragm portion 20 incorporates a reflex hammer head 30 is incorporated into the O-ring 26. The O-ring 26 is formed of an elastic material and includes a rim gripping portion 31 which slips over the rim 24 of the diaphragm portion 20 and secures the membrane 23 and the integral reflex hammer head 30 to the chest piece 14. The present invention may thus be supplied as a complete stethoscope or an ordinary stethoscope having an ordinary diaphragm membrane may be easily retrofitted to add the reflex hammer function by replacing the ordinary O-ring with the O-ring 26 incorporating the reflex hammer head 30 of the present invention.

In order to completely convert a stethoscope for use as a reflex hammer, it is necessary to provide a rigid handle, since the rubber tubing 12 of the stethoscope is too flexible to serve this function. Accordingly, as shown in FIGS. 1–7, in the preferred embodiment of the invention, a penholder 40 is rigidly affixed to the stethoscope 10 in proximity to the chest piece 14. The connection between the penholder 40 and the chest piece 14 may be made by any of a number of means that would be well understood by one skilled in the art. For example, the penholder 40 may be attached by clamps or clips around the connecting tube 15, which thus rigidly affixes the penholder 40 to the chest piece 14 and thus to the reflex hammer head 30. The penholder 40 is provided with a pen receptacle 44. A pen 41 inserted into the receptacle 44 of the penholder 40 thus provides a rigid handle for the reflex hammer function. It should be understood that the penholder 40 may be positioned to either side of the reflex hammer head 30 to accommodate left and right handed examiners.

Figure 5:
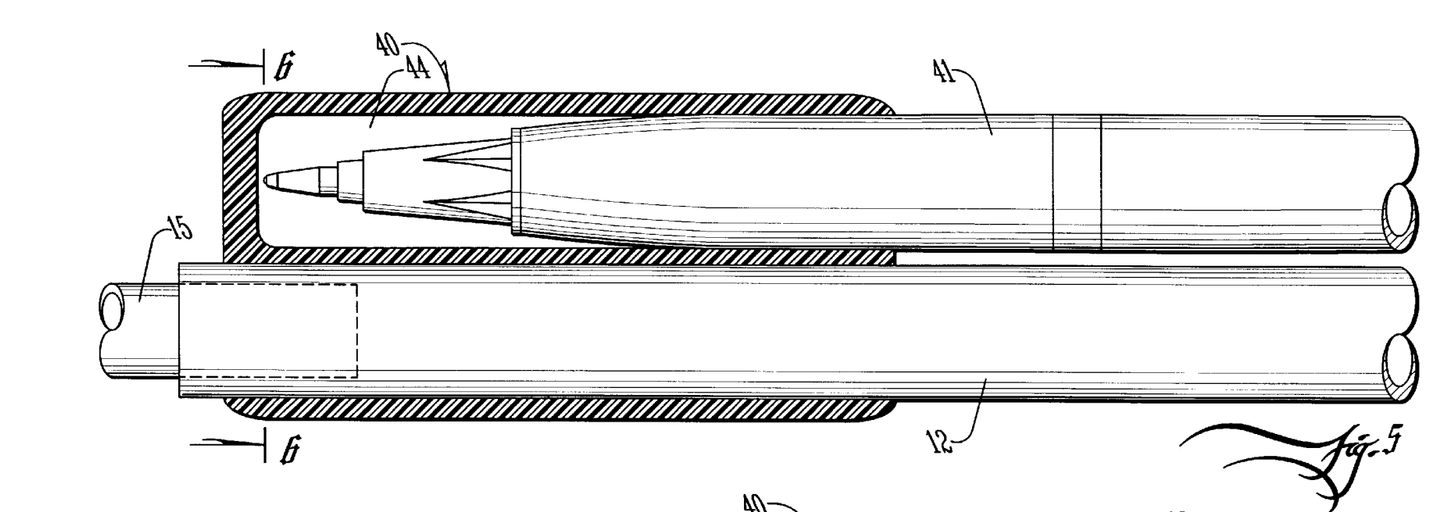
FIG. 5 is a sectional view of the penholder and pen taken along the line 5—5 of FIG. 2.

As an added feature, the pen 41 may be provided with a penlight 42 operated by a switch 43 so that the combined instrument also provides that function in addition to providing a writing pen, a reflex hammer and a stethoscope.

FIGS. 8–11 illustrate one embodiment of the invention in which the penholder 40 comprises an elastic material and includes a cylindrical space 45 sized to firmly grip the flexible tubing 12. A longitudinal slit 46 allows the flexible tubing 12 to be inserted into the cylindrical space 45 where it is firmly held by the penholder 40. It is desirable that the penholder 40 be positioned so that at least a portion of the connecting tube 15 protrudes into the cylindrical space 45 so that the penholder 40 and the chest piece 14 act as a single integral unit.

FIGS. 12–15 illustrate an alternative embodiment of the penholder 40 in which the penholder 40 is attached to the flexible tubing 12 by one or more clamps 50. Each clamp 50 comprises two identical sections 51 hinged together along one side at a hinge 52. Each section 51 comprises a pair of half-round portions 53 which are sized to firmly grip the penholder 40 and the flexible tubing 12. Opposite to the hinge 52 the sections 51 are provided with flanges 54. At least one of the flanges is provide with an adhesive pad 55 on an inner side. The two sections 51 are locked together by pressing the flanges 54 together until the adhesive pad 55 adheres to the opposite flange.

FIGS. 16–19 illustrate another means by which the penholder 40 is fastened to the flexible tubing 12 by a clamp 50 where the inside surfaces of the sections 51 are provided with additional adhesive pads 56 that adhere directly to the penholder 40 and the flexible tubing 12 so as to provide greater strength to the combination when assembled.

Figure 20:
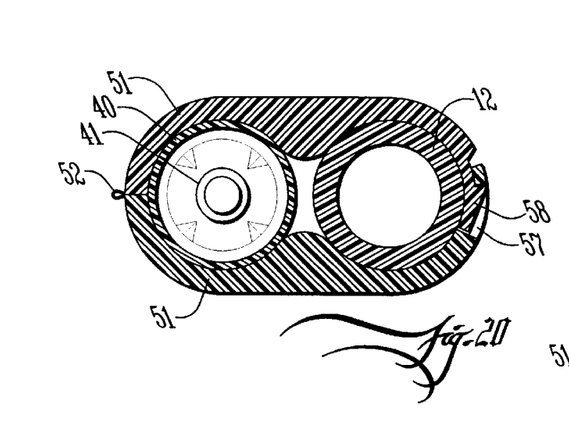
FIG. 20 is a sectional view analogous to FIG. 19.
Figure 21:
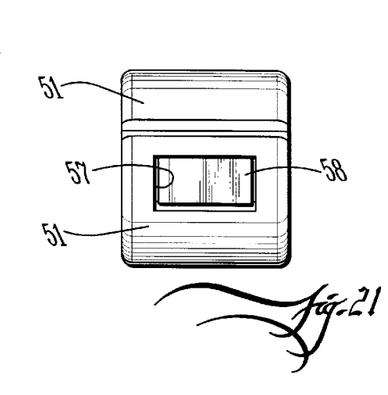
FIG. 21 is a side elevational view of FIG. 20 showing the hinged clamp locked into a closed position by the snap-on clip.
Figure 22:
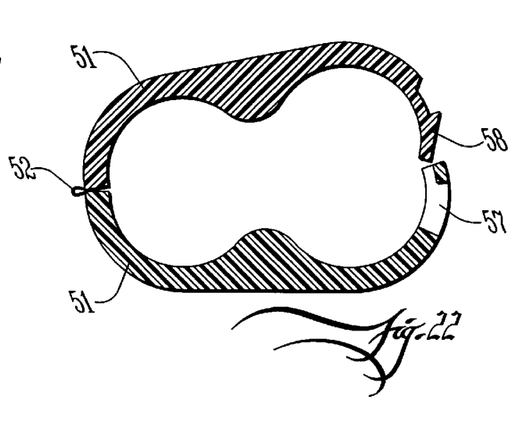
FIG. 22 is a sectional view analogous to FIG. 18.

FIGS. 20–22 illustrate another means for fastening the penholder 40 to the flexible tubing 12. An opening 57 is disposed to received a snap 58 which locks into the opening 57 when the sections 51 are closed.

Clamps of the types described above that are made of plastic material so that they can be molded in a single piece with an integral plastic hinge are known in the art and would be suitable for the practice of the present invention. The present invention is adaptable to stethoscopes of various sizes, both adult and pediatric.

The present invention has been described with reference to certain preferred and alternative embodiments that are intended to be exemplary only and not limiting to the full scope of the present invention as set forth in the appended claims.

What is claimed is:

1. A medical examining instrument, comprising:
    a stethoscope comprising a chest piece having a diaphragm portion and a bell portion operatively connected to a rigid connecting tube, a flexible tubing section connected to said rigid connecting tube, a yoke connected to a pair of ear pieces and to said flexible tubing section;
    said diaphragm portion having a mouth surrounded by a rim and further comprising an elastic o-ring securing a diaphragm membrane covering said mouth; said elastic o-ring further comprising an elastic reflex hammer head and an elastic rim-gripping portion for elastically attaching said o-ring to said mouth of said diaphragm portion;
    a rigid handle; and
    means for affixing said rigid handle to said chest piece.

2. The instrument of claim 1, wherein said handle comprises a pen and a penholder having means for receiving said pen.

3. The instrument of claim 2, wherein said pen further comprises a penlight.

4. An elastic o-ring for retrofitting a stethoscope with a reflex hammer function, the stethoscope of the type having a chest piece with a diaphragm portion and a bell portion operatively connected to a rigid connecting tube, a flexible tubing section connected to the rigid connecting tube, a yoke connected to a pair of ear pieces and to the flexible tubing section, and the diaphragm portion having a mouth surrounded by a rim over which a diaphragm membrane is disposed, comprising:
    an elastic o-ring further comprising an elastic reflex hammer head and an elastic rim-gripping portion for elastically attaching said diaphragm membrane to said mouth of said diaphragm portion.

5. A kit for retrofitting a stethoscope with a reflex hammer, function, the stethoscope of the type having a chest piece with a diaphragm portion and a bell portion operatively connected to a rigid connecting tube, a flexible tubing section connected to the rigid connecting tube, a yoke connected to a pair of ear pieces and to the flexible tubing section, the diaphragm portion having a mouth surrounded by a rim over which a diaphragm membrane is disposed, comprising:
    an elastic o-ring further comprising an elastic reflex hammer head and an elastic rim-gripping portion for elastically attaching said diaphragm membrane to said mouth of said diaphragm portion;
    a rigid handle; and
    means for affixing said rigid handle to said chest piece.

6. The instrument of claim 5, wherein said handle comprises a pen and a penholder having means for receiving said pen.

7. The instrument of claim 6, wherein said pen further comprises a penlight.

* * * * *